US010500011B2

(12) United States Patent
Tan et al.

(10) Patent No.: US 10,500,011 B2
(45) Date of Patent: Dec. 10, 2019

(54) ILLUMINATION DEVICE FOR ILLUMINATING A BODY CAVITY IN A SURGICAL SPACE

(71) Applicant: SINGAPORE HEALTH SERVICES PTE LTD, Singapore (SG)

(72) Inventors: Ngian Chye Tan, Singapore (SG); Wah Siew Tan, Singapore (SG); Min Hoe Chew, Singapore (SG); Hiang Khoon Tan, Singapore (SG); Pankaj Pandurang Sunkeri, Sunnyvale, CA (US); Siang-Long Richard Lieu, Singapore (SG); Wei Ling Fiona Loke, Singapore (SG); Iyer Narayanan Gopalakrishnan, Singapore (SG)

(73) Assignee: SINGAPORE HEALTH SERVICES PTE LTD, Singapore (SG)

( * ) Notice: Subject to any disclaimer, the term of this patent is extended or adjusted under 35 U.S.C. 154(b) by 44 days.

(21) Appl. No.: 15/573,919

(22) PCT Filed: May 17, 2016

(86) PCT No.: PCT/SG2016/050231
§ 371 (c)(1),
(2) Date: Nov. 14, 2017

(87) PCT Pub. No.: WO2016/186578
PCT Pub. Date: Nov. 24, 2016

(65) Prior Publication Data
US 2018/0353257 A1 Dec. 13, 2018

(30) Foreign Application Priority Data

May 19, 2015 (SG) .............................. 10201503943S

(51) Int. Cl.
*A61B 90/30* (2016.01)
*A61B 90/00* (2016.01)
*A61B 17/00* (2006.01)

(52) U.S. Cl.
CPC ........ *A61B 90/30* (2016.02); *A61B 17/00234* (2013.01); *A61B 90/36* (2016.02);
(Continued)

(58) Field of Classification Search
CPC .... A61B 17/00234; A61B 2017/00286; A61B 2017/00907; A61B 2017/00929; A61B 2090/0813; A61B 90/30; A61B 90/36
See application file for complete search history.

(56) References Cited

U.S. PATENT DOCUMENTS 3,042,022 A * 7/1962 Sheldon ............. A61B 1/00165
362/139
9,326,668 B1 5/2016 Rebella et al.
(Continued)

FOREIGN PATENT DOCUMENTS

ES 1129280 10/2014
WO 0207632 1/2002
(Continued)

OTHER PUBLICATIONS

International Application No. PCT/SG2016/050231, International Search Report and Written Opinion, dated Aug. 23, 2016.

*Primary Examiner* — Robert J May
*Assistant Examiner* — Leah Simone Macchiarolo
(74) *Attorney, Agent, or Firm* — Kilpatrick Townsend & Stockton LLP

(57) ABSTRACT

The present disclosure relates to an illumination device for illuminating a body cavity in a surgical space during a surgical procedure. The illumination device comprises: a flexible elongated member comprising a proximal end portion and a distal end portion; an illumination module disposed at the distal end portion of the flexible elongated member, the illumination module comprising a set of lighting elements for emitting light; and a control module disposed at the proximal end portion of the flexible elongated member, the control module comprising a set of user input elements for controlling the set of lighting elements of the illumination module, wherein the illumination module is moveable with the flexible elongated member to an illumination position in the surgical space, such that light from the set of lighting elements is emitted into the body cavity for illumination thereof; and wherein the flexible elongated member is configurable for maintaining the illumination module at said illumination position in the surgical space when the control module is disposed on a fixed structure.

20 Claims, 4 Drawing Sheets

(52) U.S. Cl.
CPC ............ *A61B 2017/00283* (2013.01); *A61B 2017/00907* (2013.01); *A61B 2017/00929* (2013.01); *A61B 2090/0813* (2016.02); *A61B 2090/309* (2016.02)

(56) References Cited

U.S. PATENT DOCUMENTS

| | | |
|---|---|---|
| 2001/0007051 A1 | 7/2001 | Nakashima et al. |
| 2005/0154262 A1 | 7/2005 | Banik et al. |
| 2007/0002582 A1* | 1/2007 | Burwell .................. A61N 5/062 362/572 |
| 2007/0185386 A1 | 8/2007 | Cheng et al. |
| 2011/0028790 A1 | 2/2011 | Farr et al. |
| 2012/0041267 A1 | 2/2012 | Benning et al. |
| 2012/0265184 A1* | 10/2012 | Sliwa .................... A61B 5/0084 606/15 |

FOREIGN PATENT DOCUMENTS

| | | |
|---|---|---|
| WO | 2004030526 | 4/2004 |
| WO | 2006074078 | 7/2006 |

\* cited by examiner

ILLUMINATION DEVICE FOR ILLUMINATING A BODY CAVITY IN A SURGICAL SPACE

TECHNICAL FIELD

The present disclosure generally relates to an illumination device. More particularly, aspects of the present disclosure are directed to an illumination device used in the field of surgery, specifically for illuminating a patient's/subject's/person's body cavity in a surgical space during a surgical procedure.

BACKGROUND

Surgical procedures such as medical examinations and operations performed on patients/subjects/persons often require assistive illumination or lighting to improve visualization by surgeons/clinicians/doctors/users, thereby mitigating risk of complications or even accidents during the surgical procedure.

Currently, operating theatres are equipped with different types of devices for providing assistive illumination while conducting the surgical operations. One example is an overhead surgical light apparatus. However, the overhead surgical light apparatus may not be able to provide illumination or lighting at the desired intensity and location because the illumination may be blocked by another object, or it may be difficult to position the illuminating elements or luminaries to direct illumination into body cavities that are too deep. Particularly for surgical procedures on patients or subjects with deep and narrow body cavities, the surgical access region is narrow and the need for improved illumination in the body cavities is significant. If the body cavity is inclined at an angle relative to the horizontal, i.e. an oblique body cavity, light from the overhead surgical light apparatus would not be able to penetrate into the deeper regions of the oblique body cavity. Surgeons using the overhead surgical light apparatus tend to struggle to gain proper visualization of the surgical space and the body cavity therein.

There are various devices that are more portable and can be deployed to improve or enhance illumination in body cavities. One common device is a head-mounted lighting device, also known as surgeon headlights or headlamps. The headlamp is mounted on the surgeon's head as a separate device, or may be mounted on another device on the surgeon's head. However, there is a tendency for the headlamp to move when the surgeon moves his head. In this way, if the surgeon looks up to speak to another surgical team member or for any other reason, the correct or desired location to be visualized may not always be adequately illuminated for the other surgical team members. Further, headlamps tend to have very focused and narrow illumination which enables the surgeon to see one area of the patient's body cavity quite clearly. But when the surgeon looks away—moving his eyes but not his head—from said area to focus on surrounding body tissues, the field of illumination does not change, causing the surgeon to have difficulty in adjusting his eyes to the body cavity's environment. This may eventually cause the surgeon to find it challenging to identify the important anatomical structures. Headlamps may also require heavy, cumbersome batteries. The design and usage methods of headlamps are often not ergonomic leading to their being cumbersome in use. Headlamps may require the surgeon's head to be angled awkwardly in order to better aim the light at a part of the surgical site. Prolonged use of headlamps can cause discomfort or strain in the neck and shoulder regions.

Some lighting devices are attachable to surgical instruments to provide assistive lighting at the surgical sites being operated with the surgical instruments. One example of surgical instruments are retractors for separating the edges of a surgical incision or wound, e.g. widening a body cavity. These attachable lighting devices tend not to be able to illuminate effectively the areas surgeons need to visualize because the surgical instruments may not be placed or directed where the light is required. For example, retractors are used to retract tissues to allow surgeons to have a wider operating space, which means that the retractors are positioned at the edge of the operating space, and thus can only illuminate the region near the edge of the operating space. These lighting devices attachable to retractors cannot provide correctly focused and adequate lighting in the body cavity; as the lighted devices do not always direct the light where it is needed.

An example of a lighting device or illumination device that is attachable to surgical instruments is disclosed in United States patent publication US 2008/0266840. Particularly, US 2008/0266840 discloses a surgical illumination device (10) that can be attached to a retractor (70). Some of the aforementioned problems regarding attachable lighting devices are relevant here as well. For example, the direction of lighting from the surgical illumination device (10) is restricted to the direction whereat the retractor (70) is pointing. Once the retractor (70) is inserted into a body cavity, the direction of illumination tends to be downwards at the peripheral surface of the body cavity. This would only allow the lower region of the body cavity to be illuminated, thus failing to uniformly illuminate the entire body cavity.

Therefore, in order to address or alleviate at least one of the aforementioned problems and/or disadvantages, there is a need to provide an illumination device for illuminating a body cavity, in which there is at least one or some improved features over the prior art.

SUMMARY

According to an aspect of the present disclosure, there is provided an illumination device for illuminating a body cavity in a surgical space during a surgical procedure. The illumination device comprises: a flexible elongated member comprising a proximal end portion and a distal end portion; an illumination module disposed at the distal end portion of the flexible elongated member, the illumination module comprising a set of lighting elements for emitting light; and a control module disposed at the proximal end portion of the flexible elongated member, the control module comprising a set of user input elements for controlling the set of lighting elements of the illumination module, wherein the illumination module is moveable with the flexible elongated member to an illumination position in the surgical space, such that light from the set of lighting elements is emitted into the body cavity for illumination thereof; and wherein the flexible elongated member is configurable for maintaining the illumination module at said illumination position in the surgical space when the control module is disposed on a fixed structure.

An advantage of the present disclosure is that the illumination device can be used to provide assistive or additional illumination to a body cavity for improved visualization. The illumination module may be positioned inside or near the body cavity to enhance illumination effects therein. The proximity of the illumination module to the body cavity provides more homogenous and uniform lighting to the body cavity. Particularly for deep and narrow cavities, the illumination device can provide better illumination in the deeper regions of the body cavity. Further, the illumination module can be stably maintained at the desired illumination position by the flexible elongated member without being attached to a surgical instrument, as disclosed in the prior art. This advantageously allows the illumination device to be used on its own without relying on external instruments.

An illumination device for illuminating a body cavity according to the present disclosure is thus disclosed hereinabove. Various features, aspects, and advantages of the present disclosure will become more apparent from the following detailed description of the embodiments of the present disclosure, by way of non-limiting examples only, along with the accompanying drawings in which like numerals represent like components.

DETAILED DESCRIPTION

Figure 1:
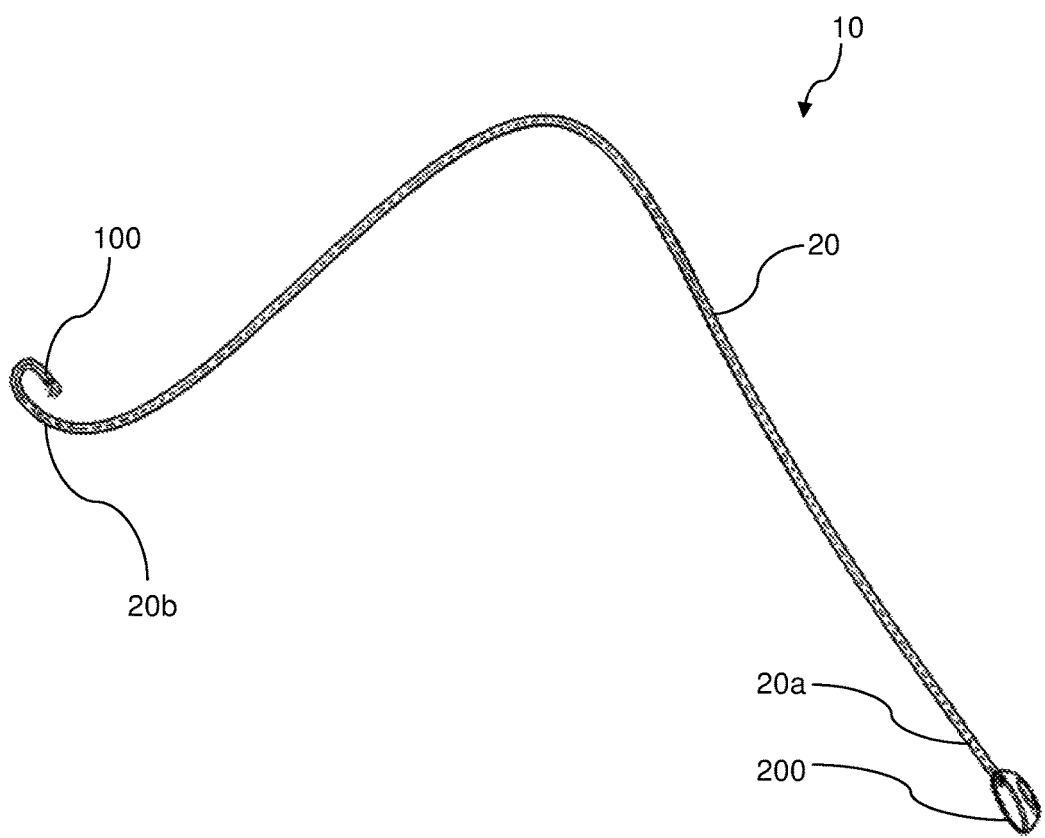
FIG. 1 is an illustration of an illumination device for illuminating a body cavity, in accordance with representative embodiments of the present disclosure.

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in a FIG. or associated text is understood to mean "and/or" unless otherwise indicated. The recitation of a particular numerical value or value range herein is understood to include or be a recitation of an approximate numerical value or value range. With respect to recitations herein directed to dimensional or numerical comparisons or equivalence, reference to the terms "generally", "approximately", or "substantially" is understood as falling within +/−20%, +/−15%, +/−10%, +/−5%, or +/−0% of a representative/example comparison, or a specified or target value or value range.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions. In general, an element of a set can include or be a system, an apparatus, a device, a structure, an object, a process, a physical parameter, or a value depending upon the type of set under consideration.

For purposes of brevity and clarity, descriptions of embodiments of the present disclosure are directed to an illumination device for illuminating a body cavity in a surgical space during a surgical procedure, in accordance with the drawings in FIG. 1 to FIG. 5. The drawings may not be illustrated to scale and certain components can be shown in generalized or schematic form and identified by commercial designations in the interest of clarity and conciseness. While aspects of the present disclosure will be described in conjunction with the embodiments provided herein, it will be understood that they are not intended to limit the present disclosure to these embodiments. On the contrary, the present disclosure is intended to cover alternatives, modifications and equivalents to the embodiments described herein, which are included within the scope of the present disclosure as defined by the appended claims. Furthermore, in the following detailed description, specific details are set forth in order to provide a thorough understanding of the present disclosure. However, it will be recognized by an individual having ordinary skill in the art, i.e. a skilled person, that the present disclosure may be practiced without specific details, and/or with multiple details arising from combinations of aspects of particular embodiments. In a number of instances, well-known systems, methods, procedures, and components have not been described in detail as not to unnecessarily obscure aspects of the embodiments of the present disclosure.

In representative or exemplary embodiments of the present disclosure, an illumination device 10 for illuminating a body cavity (not shown) in a surgical space during a surgical procedure is described hereinafter. Although embodiments of the present disclosure are described in relation to body cavities for surgical purposes, it would be readily understood by a person having ordinary skill in the art that the illumination device 10 may be used for illumination of cavities/holes/orifices in a non-surgical or non-medical environment.

With reference to FIG. 1, the illumination device 10 comprises a flexible elongated member 20, an illumination module 100, and a control module 200. In some embodiments, the flexible elongated member 20 is a selectively deformable shape-retaining elongated structure having an extended length, e.g. tubular structure, member, cylinder, etc. The elongated structure can be selectively deformed by a user and the elongated structure can retain its deformed shape even after the user releases it. In some other embodiments, the flexible elongated member 20 may be a flexible cable 20, tube, or any flexible hollow/tubular member having an extended length as readily known to the skilled person, wherein such, e.g. flexible cable 20, is yieldably adjustable so that it can maintain or retain the shape into which it is bent/deformed. The flexible cable 20 comprises a proximal end portion 20a and a distal end portion 20b at opposing ends thereof. The illumination module 100 is disposed at the distal end portion 20b and the control module 200 is disposed at the proximal end portion 20a.

The illumination module 100 comprises a set of lighting elements 102 for emitting light. The illumination module 100 is moveable with the flexible cable 20 to an illumination position in the surgical space. The term "surgical space" as used herein may refer to the spatial region where a body cavity of a patient/subject resides or is located, or may alternatively refer to the spatial region within such a body cavity, such that a user, e.g. surgeon or clinician, can use the illumination device 10 to provide optimum and/or enhanced illumination to or inside the body cavity. The term "body cavity" as used herein refers to an opening or orifice in the patient's/subject's body which may be natural, e.g. mouth, or surgically made such as through surgical incisions during surgical procedures or operations.

Figure 2A:
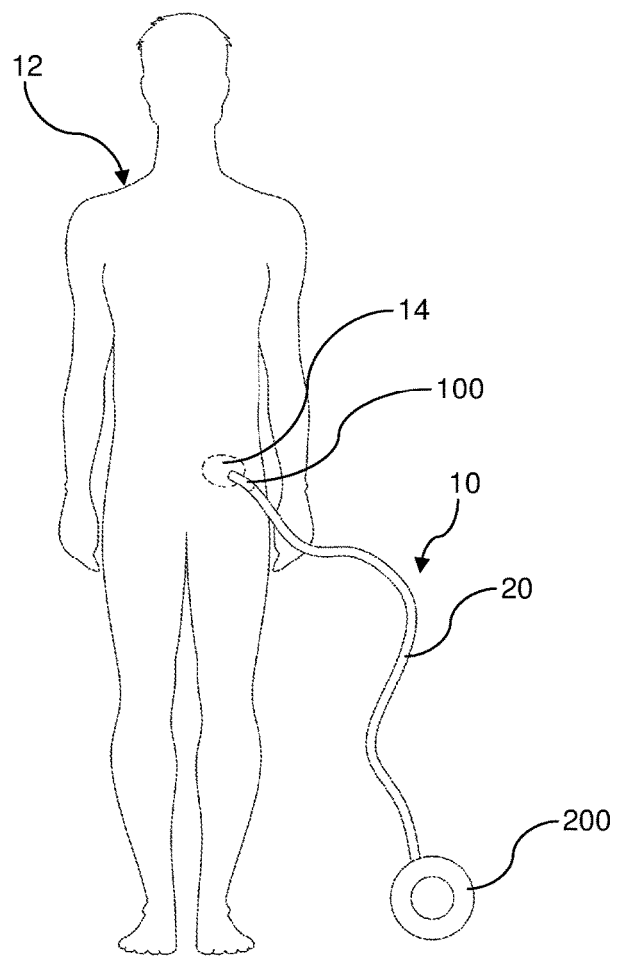
FIG. 2A is an illustration of a frontal view of a person with the illumination device of FIG. 1, in accordance with representative embodiments of the present disclosure.
Figure 2B:
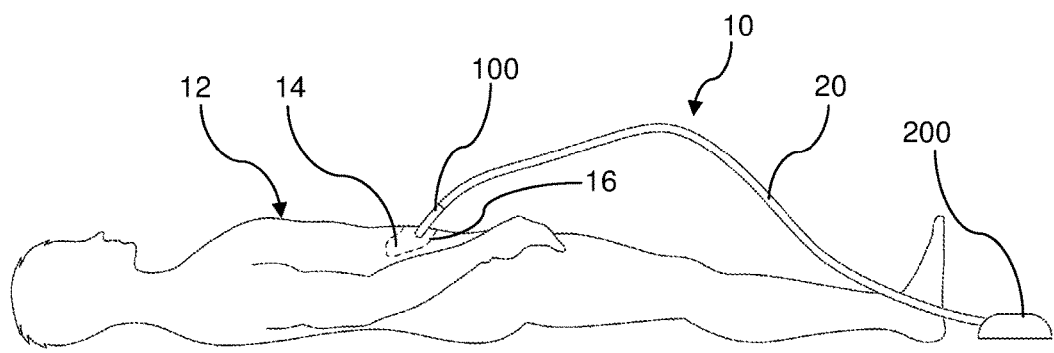
FIG. 2B is an illustration of a side view of a person with the illumination device of FIG. 1, in accordance with representative embodiments of the present disclosure.

An example of how the illumination device 10 is used with a patient 12, or patient's body, for illuminating a body cavity 14 is shown in FIG. 2A and FIG. 2B, which respectively illustrate an anterior/frontal and lateral/side view, of the patient 12. The illumination device 10, particularly the control module 200, is positioned or rested on a fixed structure, e.g. the drapes placed over the patient 12 or operating bed where the patient 12 is resting on, and the illumination module 100 is inserted into the body cavity 14 of the patient's body 12.

As the illumination module 100 is attached to the flexible cable 20, flexure or bending of the flexible cable 20 is able to move the illumination 100 to the desired position. The illumination position may reside outside of the body cavity 14, e.g. above the body cavity 14 such that light from the set of lighting elements 102 is emitted into the body cavity 14 for illumination thereof. The illumination position may alternatively reside within the body cavity 14, such that the illumination module 100 can be positioned in any suitable manner inside the body cavity 14 for internal illumination thereof, i.e. the illumination module 100 is adapted to be inserted into or received by the body cavity 14 for residing therein for illuminating substantially the entire internal spatial region of the body cavity 14.

For hygiene purposes, the illumination device 10 may be sterilized and packaged beforehand for use during the surgical procedure and for disposal after. Alternatively, the illumination device 10 can be cleaned and re-used after each surgical procedure. The illumination module 100 may be sterilized, e.g. with gamma radiation, prior to insertion into the body cavity 14 and moving to the illumination position within the body cavity 14. The flexible cable 20 may be bent in a manner that facilitates the illumination module 100 to be fixedly located at the desired illumination position within the body cavity 14. For example, the illumination module 100 can be positioned at the desired illumination position by dangling inside the body cavity 14 (as more clearly shown in FIG. 2B), whereby the flexible cable 20 can be bent in such a way that the profile of the illumination module 100 and the distal end portion 20b of the flexible cable 20 conform to the peripheral profile of the body cavity 14. The peripheral profile of the body cavity 14 refers to the lateral or side surface 16 inside the body cavity 14 that is formed at the surface of the patient's body 12 by virtue of a surgical incision or procedure. More specifically, the illumination module 100 and distal end portion 20b is inserted into the body cavity 14 along the direction of the depth thereof and adjacent to (or almost touching) the side surface 16 thereof. In some surgeries, the illumination module may also touch the side surface 16 of the body cavity 14.

In some surgical procedures, conventional illumination techniques, e.g. overhead lighting apparatus, do not provide adequate lighting for the surgeons. Such surgical procedures include but are not limited to operations at body cavities in the head and neck region (e.g. resection of throat cancers), colorectal (e.g. resection of bowel cancers), obstetrics and gynaecology, spinal and urology spaces. There is greater lighting inadequacy if the surgical sites contain deep and narrow body cavities. Deep and narrow body cavities generally refer to body cavities having their length/depth dimension larger than their diameter/width dimension, similar to a tunnel. Deep and narrow body cavities can be seen in incisions made at an oblique angle or vertically downward into the body. FIG. 2B illustrates a body cavity 14 being inclined at an oblique angle into the patient's body 12. The use of the illumination device 10 is advantageous because the illumination module 100 can be inserted deeper into the body cavity 14 for providing better illumination of the internal regions of the body cavity 14. Conventional overhead lighting apparatus or headlamps could not have illuminated the deeper regions of the body cavity 14 because the light would not be able to penetrate into the body cavity 14, particularly for oblique incisions.

One method for illuminating a body cavity 14 is by inserting the illumination module 100 through an incision on the patient's body 12 leading into the body cavity 14. The illumination device 10 has a small cross-sectional diameter that facilitates its insertion into the incision. In various embodiments, the illumination module 100 has a cross-sectional diameter ranging from 1 mm to 20 mm. In a representative embodiment, the cross-sectional diameter of the illumination module 100 is preferably 10 mm. The incision on the body 12 may be a drain incision having a normal diameter of, for example but not limited to, approximately 10 mm. A drain incision is usually made to insert a drain tube to remove body fluids that may build up at the body cavity 14 after a surgical procedure or operation. The entirety of the illumination module 100 has an approximate length of, but not limited to, 10 cm, and is insertable into or able to gain access into the body cavity 14 via the incision. The illumination module 100 is thus sizeable in a manner to provide a small footprint that enables it to be deployed in narrow body cavities. The entire illumination device 10 is also lightweight at approximately 30 g to 50 g so that it can be conveniently moved around for use in surgical procedures, particularly those involving deep and narrow body cavities. In some situations, a portion of the flexible cable 20, particularly its distal end portion 20b, may also be insertable into the body cavity 14, especially if the body cavity 14 is deep, together with the illumination module 100.

The illumination device 10 is configured to stably maintain or configurable for stably maintaining its positioning and repositioning during usage in a surgical procedure, and enables easy manoeuvring of the illumination module 100. Particularly, when the control module 200 is disposed on a fixed structure, the flexible cable 20 is configured to maintain or configurable for maintaining the illumination module at the illumination position in the surgical space. The control module 200 may be affixed in the perioperative sterile area, such as the drapes or operating bed, to provide a fixed position for enabling movement of the flexible cable 20, and consequently the illumination module 100, relatively thereto. The control module 200 may be sterilized prior to being placed on the drapes or operating bed. The flexible cable 20 is able to withstand bending angles of 20° to 340° without kinking or breaking. In this manner, the flexible cable 20 is yieldably adjustable so that it can maintain or retain the shape into which it is bent and the associated bending angle, thereby maintaining the illumination module 100 at the desired illumination position. The illumination module 100 will remain at the desired illumination position for as long as the user does not move the illumination device 10.

In some alternative embodiments, the illumination device 10 may include an anchoring mechanism for maintaining the illumination module 100 at the desired illumination position. The anchoring mechanism enables the illumination device 10, particularly the distal end portion 20b of the flexible cable 20, to be affixed or secured to a fixed structure or an external body, e.g. the drapes or operating bed. The anchoring of the flexible cable 20 enables the illumination module 100 to be maintained at a fixed position for illuminating the surgical site where the body cavity 14 is located. The anchoring mechanism may also affix/secure the flexible cable 20 to the surgical site, particularly the area of the patient's body 12 surrounding the body cavity 14. Broadly, the anchoring mechanism may be located at the illumination module 100 or the flexible cable 20 for anchoring portions of the illumination device 10 to an external body.

Figure 3A:
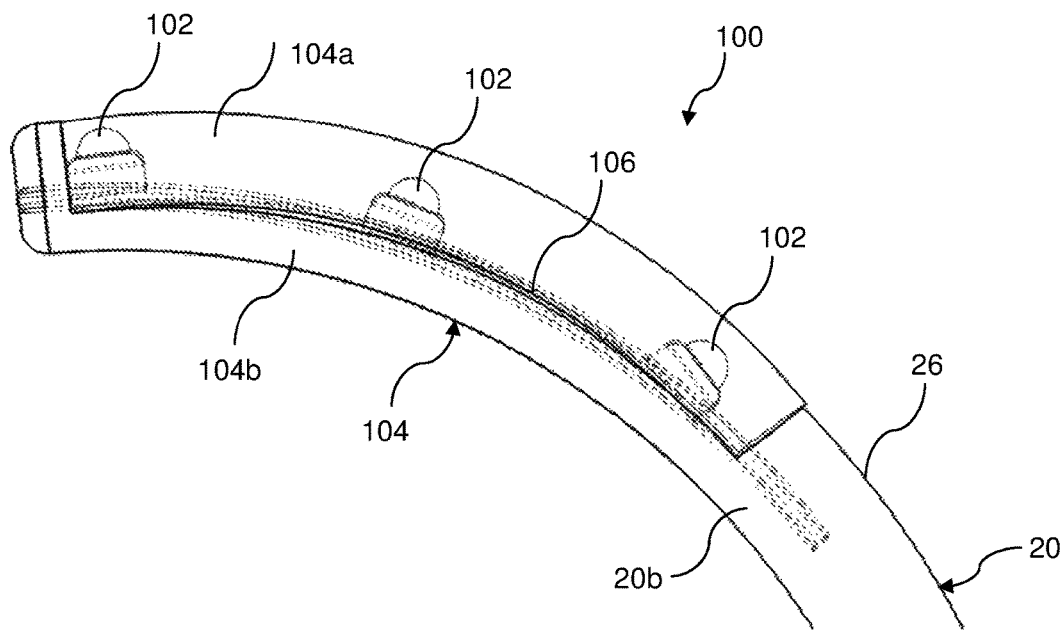
FIG. 3A is an illustration of an illumination module of the illumination device of FIG. 1, in accordance with one embodiment of the present disclosure.
Figure 3B:
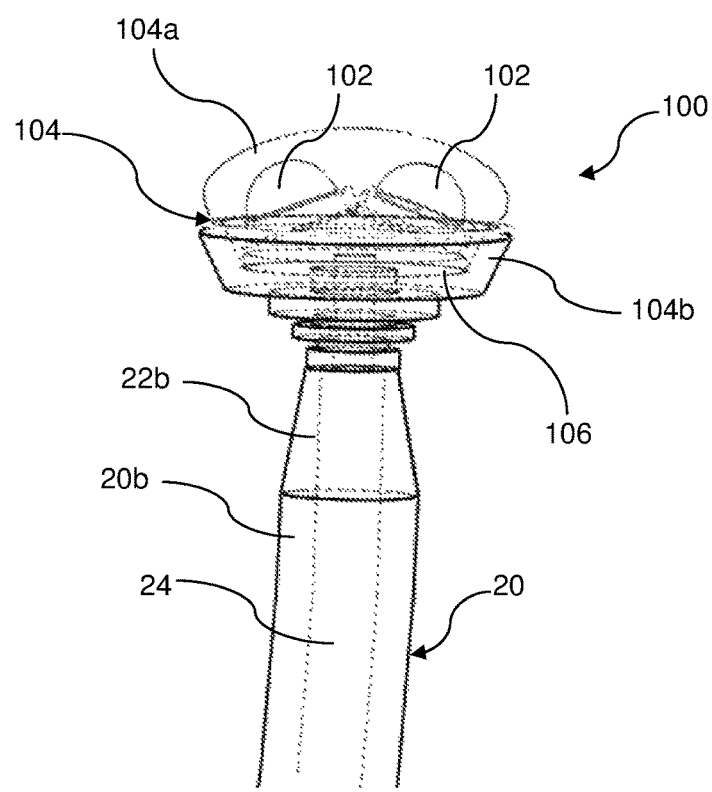
FIG. 3B is an illustration of an illumination module of the illumination device of FIG. 1, in accordance with another embodiment of the present disclosure.

A representative embodiment of the illumination module 100 is shown in FIG. 3A while an alternative embodiment of the illumination module 100 is shown in FIG. 3B.

With reference to both FIG. 3A and FIG. 3B in general, each lighting element 102 in the illumination module 100 may be a light-emitting diode (LED) operating in parallel with an LED driver module. Examples of LEDs include, but are not limited to, the OSLON® SSL from OSRAM. Each lighting element 102 emits light at a colour temperature ranging from 4000 K to 6000 K. This translates to the light from the lighting element 102 appearing as white, cool white, or daylight colours. With illumination of these types of colours, surgeons who are using the illumination device 10 to illuminate a body cavity 14 can visualize the body tissues at the correct natural colours. If the colour temperature is below 4000 K, the light may appear as warm white or even yellowish, compromising the visualization of the correct and natural colours of the body tissues. These tissues can be diseased or non-diseased muscle, fat, fascia, and various organs. Conversely, if the colour temperature is above 6000 K, the light may appear as very cool white which can be too bright or glaring for the user. The user may not be able to clearly visualize colour contrasts of the body tissues. Thus, at the colour temperature range of 4000 K to 6000 K, the illumination from the lighting elements 102 facilitates easy and physiologically accurate colour rendering of body tissues so as to aid the surgeon during the surgical procedure.

In various embodiments, each lighting element 102 additionally emits light at an illuminance or luminous intensity ranging from 0 to 6000 lux when the lighting element 102 is placed at a distance of 5 cm to 40 cm from an illuminated surface in the body cavity 14. This illuminance range enables the user to optimally operate the illumination device 10 for a duration, e.g. between 0 to 8 hours, that is adequate to provide assistive illumination to body cavities during some of the aforementioned types of surgical procedures. It would be readily understood by the skilled person that the illuminance of each lighting element 102 can vary and different types of LEDs with various optical properties may be used depending on user requirements and ambient conditions where the illumination device 10 is used.

In embodiments of the illumination module 100 shown in FIG. 3A and FIG. 3B, each lighting element 102 emits light across a spatial distribution from a central axis through the lighting element 102. This spatial distribution of light from each lighting element or LED 102 may be in the form of a cone-like or frustoconical spatial volume spreading from the central axis which passes through a centre of the lighting element 102. It would be readily understood by the skilled person that the spatial distribution or spread of light from each lighting element or LED 102 can come in different forms, shapes, and/or sizes, depending on the inherent properties of the LED 102.

When used together in the illumination module 100, the lighting elements 102 complement one another such that the set of lighting elements 102 is able to collectively emit light across an illumination angle of at least 180°, achieving broad-beamed illumination similar to floodlights. The illumination device 10 is thus able to provide wide-field illumination (at least 180° dispersion) at the appropriate illuminance and colour temperature, allowing the user to visualize a wider spatial region in the body cavity 14 at the optimum brightness and colour rendering during the surgical procedure. As the illumination module 100 is disposed at the illumination position in the surgical space and is inside or near the body cavity 14, the proximity of the lighting elements 102 to the body cavity 14 provides more homogenous and uniform lighting thereto, similar to floodlight effects. Conventional fibre optic light has the light source located further from the surgical space and light needs to travel a longer distance along a light guide before reaching the body cavity, resulting in wastage or loss of light as the distance traveled is further. In various embodiments of the present disclosure, the set of lighting elements 102 uses LEDs disposed at the distal end portion 20b of the flexible cable 20. This allows the LEDs to be located much closer to the body cavity for providing better illumination thereto.

Further, the set of lighting elements 102 of the illumination module 100 is configurable for emitting light along multiple directions from the distal end portion 20b of the flexible cable 20. This means that the light from the lighting elements 102 is emitted along multiple different directions, thereby enabling the set of lighting elements 102 to collectively emit light across an illumination angle of at least 180°. Particularly, each lighting element 102 is configurable such that each central axis therethrough may be configured to be distinct, different, and non-parallel to at least one other central axis.

Figure 4A:
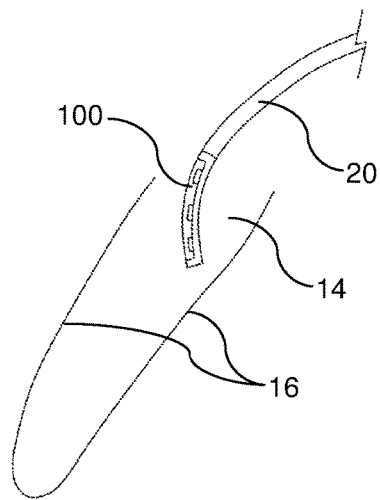
FIG. 4A is an illustration of a cross-sectional view of the body cavity inserted with the illumination module of FIG. 3A, in accordance with one embodiment of the present disclosure.

In the representative embodiment shown in FIG. 3A, there are three lighting elements 102 lengthwise positioned along the distal end portion 20b. Each lighting element 102 is configurable for emitting light in a direction that is substantially perpendicular to the longitudinal axis of the distal end portion 20b. Further, the distal end portion 20b is bendable or yieldable adjustable such that each of the three lighting elements 102 are directed toward multiple different directions. This arrangement of the lighting elements 102 provides a wide-spread combined illumination angle of at least 180°, optimizing the dispersion of light within the body cavity 14. An example of the illumination module 100 inserted into the body cavity 14 is shown in FIG. 4A, The illumination module 100 is inserted obliquely into the body cavity 14 and adjacent to a peripheral surface 16 of the body cavity 14. The illumination from the set of lighting elements 102 will be directed inwardly and deeper into the body cavity. There is thus a more effective use of the combined illumination or light emitted by the set of lighting elements 102, and the internal region of the body cavity can be more optimally illuminated. Further, by providing wide-spread illumination across a combined illumination angle of at least 180°, the illumination module 100 can provide broad-beamed illumination similar to floodlights or achieve the visual effects of floodlight illumination.

Figure 4B:
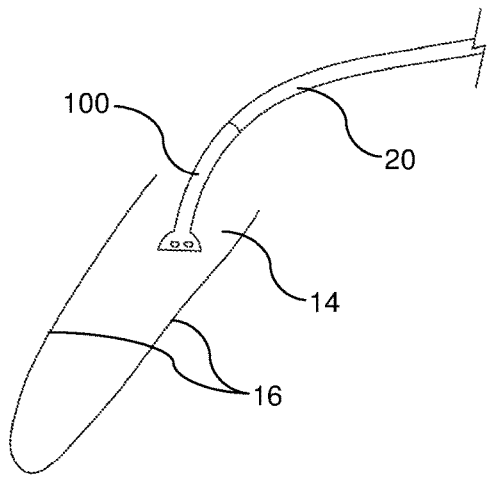
FIG. 4B is an illustration of a cross-sectional view of the body cavity inserted with the illumination module of FIG. 3B, in accordance with another embodiment of the present disclosure.

In the alternative embodiment shown in FIG. 3B, at least two lighting elements 102 are positioned at an end of the distal end portion 20b of the flexible cable 20. Each lighting element 102 is directed toward distinct or different directions. The central axis of each lighting element 102 is distinct, different, and non-parallel to the other. Specifically, each lighting element 102 is configurable for emitting light in a direction that is angled away from the longitudinal axis of the distal end portion 20b. This enables illumination from the set of lighting elements 102 to collectively disperse across a wider region, thereby achieving a combined illumination angle of at least 180°. An example of the illumination module 100 inserted obliquely into the body cavity 14 is shown in FIG. 4B. By dispersing illumination across a wide angle of at least 180°, the illumination module 100 can provide broad-beamed illumination similar to floodlights or achieve the visual effects of floodlight illumination.

In various embodiments of the present disclosure, the illumination module 100 comprises a housing or casing 104 for thermally and electrically insulating the set of lighting elements 102. The lighting elements 102 require electricity to operate and may produce heat during operation. The casing 104 provides at least one layer of thermal and electrical insulation for the set of lighting elements 102, allowing the user to safely position and use the illumination module 100 in the surgical space for illuminating the body cavity. The material of the casing 104 has thermal insulation properties that can manage the heating effect of the lighting elements 102 and bring such heating effect below a temperature threshold that could cause harm to body tissues. Particularly, the casing 104 minimizes the heating effect at potential points of contact with body tissues such that the temperature at these points of contact is not above 40° C., allowing the illumination device 10 to be safely and effectively used without possibility of harming body tissues.

The casing 104 is made of a material that can be safely deployed inside the body cavity 14 or any suitable cavity within the patient's body 12 or external location of the body 12 for the duration of the surgical procedure. For example, the casing 104 may be made of biocompatible materials or biomaterials that have been engineered to interact with biological systems for a medical purpose. Non-limiting examples of such biomaterials include polycarbonate, poly (methyl methacrylate) (PMMA), polylactic acid (PLA), acrylonitrile butadiene styrene (ABS), silicone, medical-grade titanium, medical-grade surgical stainless steel, and epoxy. Biocompatible materials are used so that the illumination module 100 inserted into the body cavity 14 does not chemically and/or biologically interact with the body tissues which can cause unwanted clinical effect, deterioration, or harm. When the illumination module 100 is inserted into the body cavity 14 during the surgical procedure, the casing 104 can substantially prevent ingress of fluids into the illumination module 100 for the duration of the surgical procedure, e.g. between 0 to 8 hours.

The casing 104 may be fabricated by means of, but not limited to, injection moulding, compression moulding, or room temperature curing. The profile of the casing 104 is such that the casing 104 has rounded/filleted surfaces and edges which prevent mechanical trauma to body tissues. The design, material, size, and/or shape of the casing 104 may vary depending on usage requirements. For example, the internal space inside the casing 104 for housing the set of lighting elements 102 may be a vacuum or may alternatively be filled with a fluid, e.g. air. The presence of fluid within the casing 104 facilitates dissipation of heat from the lighting elements 102 via convective heat transfer or convection. Further alternatively, the lighting elements 102 may be solidly encapsulated within the casing 104.

The casing 104 comprises an optically transmissive portion 104a and an optically occlusive portion 104b. The optically transmissive portion 104a is disposed at a front portion of the illumination module 100, such that light from the set of lighting elements 102 is emitted therethrough. The optically transmissive portion 104a may be removably attached or attachable to the distal end portion 20b of the flexible cable. For example, the optically transmissive portion 104a may be coupled or fastened to the distal end portion 20b using temporary means such as clips or latches as readily known to the skilled person. Removal of the optically transmissive portion 104a allows the lighting elements 102 to be repaired or replaced. Alternatively, the optically transmissive portion 104a may be permanently attached to the distal end portion 20b, such as with adhesives. Further, the optically transmissive portion 104a may comprise a set of lenses or optical elements for modifying transmission of light from the set of lighting elements to a user's eyes. The set of lenses or optical elements may further be configurable for providing homogenous and uniform illumination from the lighting elements 102 to the user's eyes. The optically occlusive portion 104b is disposed at a rear portion of the illumination module 100 to shield the user's eyes from direct illumination or light from the lighting elements 102. The optically transmissive portion 104a thus protects the user's eyes from excessively glare and enables the user to more clearly visualize the body cavity 14 and the surgical site.

The illumination module 100 further comprises a heat sink 106 housed within the casing 104. The heat sink 106 is made of a heat dissipative material, e.g. copper, aluminium, or brass. The heat sink 106 will be of an appropriate volume and shape based on the thermal conductivity of the heat dissipative material, as readily understood by the skilled person. The heat sink 106 is thermally connected to the set of lighting elements 102 for removing heat therefrom, so as to reduce the temperature at the lighting elements 102 to not more than 40° C. Particularly, the heat sink 106 assists in dissipating heat from the lighting elements 102 such that the temperature at points of contact between the casing 104 and body tissues is not above 40° C. The heat sink 106 may utilize appropriate designs that increase the thermal conductive path length between the heat-producing lighting elements 102 and the casing 104, thereby improving the efficiency of heat dissipation.

In an example as shown in FIG. 3A, three lighting elements 102 are arranged in a linear manner and are thermally connected to a heat sink 106. Alternatively, the three lighting elements 102 may be soldered to a flexible elongated printed circuit board (PCB) which also functions as the heat sink 106. The PCB or heat sink 106 can be yieldably bent together with the flexible cable 20 to the shape and angle that the user requires, such as to enable a wider illumination angle of the illumination module 100. In another example as shown in FIG. 3B, two lighting elements 102 are thermally connected to a heat sink 106. Alternatively, the two lighting elements 102 may be soldered to a rigid printed circuit board (PCB) which also functions as the heat sink 106. The two lighting elements 102 are mounted with an angle between them so that light from the two lighting elements 102 can collectively disperse across a wider region. As the PCB or heat sink 106 is structurally rigid, the angle between the two lighting elements 102 is fixed, but the separation between the two lighting elements 102 already provides the wide illumination angle of the illumination module 100.

In various embodiments of the present disclosure, the illumination module 100 is disposed at or integrally connected to the distal end portion 20b of the flexible cable 20 and the control module 200 is disposed at or integrally connected to the proximal end portion 20*a* of the flexible cable 20. The interconnection between the illumination module 100 and the flexible cable 20, as well as the interconnection between the control module 200 and the flexible cable 20, may be hermetically or non-hermetically sealed from the external environment by means of, but not limited to, ultrasonic welding or feedthrough. This enables the complete illumination device 10 to be sterilized for safe usage in the surgical procedure. The illumination device 10 may be disposed after use, or washed and re-used for the next surgical procedure.

Alternatively in some embodiments, the illumination module 100 and control module 200 may be attached/attachable to the distal end portion 20*b* and proximal end portion 20*a*, respectively. The illumination device 10 may include a proximal connector 22*a* between the control module 200 and the flexible cable 20, as well as a distal connector 22*b* between the illumination module 100 and the flexible cable 20. The control module 200 and/or illumination module 100 may be attached and removed from the flexible cable 20 via the proximal and distal connectors 22*a*, 22*b*, respectively. This enables the illumination device 10 to become modular in design and facilitates repair and replacement of individual modules, e.g. the illumination module 100 and control module 200. The proximal connector 22*a* and distal connector 22*b* may be hermetic or non-hermetic.

The flexible cable 20 may be of varying lengths depending on usage requirements. For example, if the surgical procedure occurs in an operating theatre and the patient 12 is lying on the operating bed, the flexible cable 20 may be of a length, e.g. 30 cm to 50 cm that at least allows the illumination module 100 to reach the patient's body 12 when the control module 200 is disposed on the drapes or operating bed as the fixed structure. The flexible cable 20 may be similar in size relative to the illumination module 100 such that the distal end portion 20*b* can be inserted into the body cavity 14. Particularly, the flexible cable 20 can have an outer diameter ranging from 1 mm to 20 mm. In a representative embodiment, the outer diameter of the flexible cable 20 is preferably 10 mm. The flexible cable 20 may be sterilized prior to use or before insertion into the body cavity 14 for hygiene reasons. The flexible cable 20 is yieldably adjustable for enabling easy positioning of the illumination module 100 at the desired illumination position, and is able to withstand acute bending angles without kinking or breaking. Further, as the illumination module 100 is located at the distal end portion 20*b*, repeated bending or flexing of the flexible cable 20 to acute angles will not result in decrease of illuminance or luminous intensity.

The flexible cable 20 may be made from one or more connected or unconnected sections of structural material such as metal wires or interlocking elements/couplings as readily understood by the skilled person. Some portions of the flexible cable 20 may be stiffer than others to facilitate conformance to the body anatomy, e.g. the distal end portion 20*b* may be stiffer than other portions of the flexible cable 20 as the distal end portion 20*b* is located nearer to the body cavity 14 where the illumination module 100 is used.

The flexible cable 20 includes at least one structural member therein that can provide structural support to the illumination module 100 when the illumination module 100 is moved to the illumination position in the surgical space. The structural member may be made of a material such as, but is not limited to, aluminium, copper, or brass. The structural support provided by the flexible cable 20 maintains the illumination module 100 at the illumination position when the control module 200 is disposed on a fixed structure. The flexible cable 20 enables the illumination module 100 to stably remain in the desired illumination position and provides for easy repositioning possibilities during any phase of the surgical procedure.

The flexible cable 20 also houses electrical connections between the illumination module 100 and the control module 200. The control module 200 is configurable for switching on and off the set of lighting elements 102, and for adjusting illuminance of the lighting elements 102 through these electrical connections. Alternatively or additionally, the colour temperature of the lighting elements 102 may be adjusted using the control module 200. The electrical connections can be in the form of, but not limited to, electrical wires or flexible printed circuits. The flexible cable 20 further includes an insulation layer for electrically insulating the electrical connections. The flexible cable 20 thus has a tubular profile, i.e. with hollow portion 24 as shown in FIG. 3B, for accommodating the electrical connections. The flexible cable 20 may be purchased or obtained from commonly available sources, shops, or suppliers (i.e. off-the-shelf), or may be fabricated by means of, but not limited to, injection moulding, compression moulding, or room temperature curing. The hollow portion 24 also accommodates the structural member and the insulation layer or outermost layer of the flexible cable 20 covers the structural member. The insulation layer may be made of a biocompatible material, e.g. silicone or polycarbonate (PC).

The flexible cable 20 may further comprise a heat transfer cable therein and thermally insulated by the insulation layer. The heat transfer cable is accommodated within the hollow portion 24 and is thermally connected to the heat sink 106 for conducting heat away therefrom. The efficiency of heat dissipation from the lighting elements 102 is improved due to the increase in the combined length of the heat sink 106 and the heat transfer cable, and consequently the increase in combined thermal conductivity. The heat transfer cable may be housed alongside the electrical connections and the structural member within the flexible cable 20 and protected by the external insulation layer.

Figure 5:
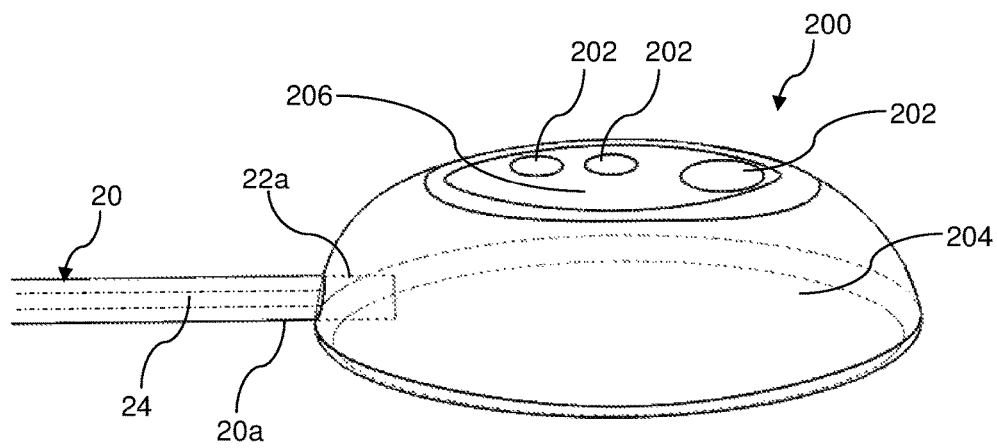
FIG. 5 is an illustration of a control module of the illumination device of FIG. 1, in accordance with representative embodiments of the present disclosure.

In various embodiments of the present disclosure with reference to FIG. 5, the control module 200 comprises a set of user input elements 202 for controlling the set of lighting elements 102 of the illumination module 100. Particularly, the set of user input elements 202 is configurable for turning on and off the lighting elements 102, and for adjusting illuminance and/or colour temperature of the lighting elements 102. The control module 200 comprises an enclosure or housing 204 for a power source as well as electronic components for powering and controlling the lighting elements 102 via electrical connections in the flexible cable 20. Alternatively, the illumination module 100 may comprise one or more power sources such as rechargeable/disposable batteries, or an inductive power circuit for powering the lighting elements 102 from within the illumination module 100. These batteries may be of a suitable capacity, continuous discharge current, and size, as readily understood by the skilled person, and may include but not limited to lithium cylindrical cells. The electronics in the control module 200 enable the user to choose the desired illuminance or luminous intensity output of the lighting elements 102 when the lighting elements 102 are placed at a distance from the illuminated surface. Examples of such electronics or electronic components in the control module 200 include, but are not limited to adaptor for converting alternating current (AC) to direct current (DC) and rectifying the overall electric circuit as appropriate, an LED driver circuit with pulse width modulation (PWM), and one or more resistors or means of controlling the amount of electric current supplied to the lighting elements 102.

The profile of the housing 204 of the control module 200 is as small and flat as possible so that it has a small footprint. The control module 200 can thus be portable and does not take up a large amount of space, e.g. when placed in the sterilized area of the surgical process. The flatness of the housing 204 allows the control module 200 to be stably placed on the operating bed. The profile of the housing 204 is such that the housing 204 has rounded/filleted surfaces and edges which allows the user to safely hold and position the control module 200. The housing 204 may be fabricated by means of, but not limited, to injection moulding, compression moulding, or room temperature curing. The control module 200 also enables the user to affix it anywhere in the perioperative sterile area to provide a fixed position for the flexible cable 20 and illumination module 100. The control module 200 can be affixed by some control module attachment means or mechanisms (not shown) so that so that the control module 200 can remain in place during the surgical process. Some examples include using spring clip, clamp, or tape to affix the control module 200 to the drapes or operating bed.

The housing 204 protects the internal circuitry and electronics of the control module 200 and of the set of user input elements 202 from exposure to the external environment. The housing 204 may be made of biocompatible materials, e.g. silicone or polycarbonate (PC). For example, the housing 204 includes a silicone membrane/sheet 206 for covering the user input elements 202 in order to prevent the internal circuit components from exposure to the external environment. The flexible nature of the silicone membrane/sheet 206 allows the user to actuate the user input elements 202 underneath without breaking or compromising the integrity of the housing 204. The silicone membrane/sheet 206 may be fused with the housing 204 by means of, but not limited to, ultrasonic welding so that the user input elements 202 can be hermetically or non-hermetically sealed from the external environment.

The set of user input elements 202 for controlling the lighting elements 102 may comprise, but is not limited to, membrane switches, magnetic switches, latching switches, and standard push buttons/pads, actuators, as readily known to the skilled person as industry standard user input elements. In some embodiments with reference to FIG. 5, the set of user input elements 202 includes a first switch for turning on and off the lighting elements 102, a second switch for adjusting the illuminance or luminous intensity of the lighting elements 102, and a third switch for adjusting the colour temperature of the lighting elements 102. The user input elements 202 may be hermetically or non-hermetically sealed inside the housing 204 in order to maintain the integrity of the control module 200 and the entire illumination device 10 during sterilization and over its operational lifetime.

In the foregoing detailed description, embodiments of the present disclosure in relation to an illumination device for illuminating a body cavity in a surgical space during a surgical procedure are described with reference to the provided figures. Although various embodiments are described in relation to body cavities for surgical purposes, it would be readily understood by the skilled person that the illumination device may be used for illumination of cavities/holes/orifices in a non-surgical or non-medical environment.

The description of the various embodiments herein is not intended to call out or be limited only to specific or particular representations of the present disclosure, but merely to illustrate non-limiting examples of the present disclosure. The present disclosure serves to address at least some of the mentioned problems and issues associated with the prior art. Although only some embodiments of the present disclosure are disclosed herein, it will be apparent to the skilled person in view of the present disclosure that a variety of changes and/or modifications can be made to the disclosed embodiments without departing from the scope of the present disclosure. The scope of the present disclosure as well as the scope of the following claims is not limited to embodiments described herein.

The invention claimed is:

1. An illumination device for illuminating a body cavity in a surgical space during a surgical procedure, the illumination device comprising:
   a flexible elongated member comprising a proximal end portion and a distal end portion;
   an illumination module disposed at the distal end portion of the flexible elongated member, the illumination module comprising a set of lighting elements for emitting light; and
   a control module disposed at the proximal end portion of the flexible elongated member, the control module comprising a set of user input elements for controlling the set of lighting elements of the illumination module,
   wherein the illumination module is moveable with the flexible elongated member to an illumination position in the surgical space, such that light from the set of lighting elements is emitted into the body cavity for illumination thereof; and
   wherein
   (a) the flexible elongated member is made of a material adapted to allow the flexible elongated member and the illumination module disposed therein to withstand bending angles up to 340° without kinking or breaking and to maintain the illumination module at said illumination position in the surgical space when the control module is disposed on a fixed structure, and the flexible elongated member is adjustable such that each lighting element is directed toward a different direction for improved visualisation;
   (b) each lighting element emits light at a colour temperature ranging from 4000 K to 6000K, and
   (c) the illumination device is not attached to a surgical instrument.

2. The illumination device of claim 1, wherein the set of lighting elements is configurable for emitting light along multiple directions from the distal end portion of the flexible elongated member.

3. The illumination device of claim 2, wherein the set of lighting elements is configurable for collectively emitting light across an illumination angle of at least 180°.

4. The illumination device of claim 1, wherein the set of lighting elements comprises at least two lighting elements positioned lengthwise along the distal end portion of the flexible elongated member.

5. The illumination device of claim 4, wherein the distal end portion of the flexible elongated member is bendable for configuring the least two lighting elements to collectively emit light across an illumination angle of at least 180°.

6. The illumination device of claim 1, wherein the set of lighting elements comprises at least two lighting elements positioned at an end of the distal end portion of the flexible elongated member.

7. The illumination device of claim 6, wherein each lighting element from the at least two lighting elements is directed toward different directions, enabling light from the at least two lighting elements to be collectively emitted across an illumination angle of at least 180°.

8. The illumination device of claim 1, wherein said illumination position of the illumination module resides within the body cavity for internally illuminating the body cavity.

9. The illumination device of claim 8, wherein the flexible elongated member is bendable to conform to a peripheral profile of the body cavity for maintaining the illumination module at said illumination position within the body cavity.

10. The illumination device of claim 1, wherein the illumination module is sterilizable prior to use.

11. The illumination device of claim 1, wherein the illumination module comprises a casing for thermally and electrically insulating the set of lighting elements.

12. The illumination device of claim 11, wherein the casing comprises an optically transmissive portion.

13. The illumination device of claim 12, wherein the optically transmissive portion is removably attached to the distal end portion of the flexible elongated member.

14. The illumination device of claim 12, wherein the optically transmissive portion comprises a set of lenses for modifying transmission of light from the set of lighting elements to a user's eyes.

15. The illumination device of claim 11, wherein the casing comprises an optically occlusive portion for shielding a user's eyes from light emitted from the set of lighting elements.

16. The illumination device of claim 1, wherein the illumination module comprises a heat sink thermally connected to the set of light elements for removing heat therefrom.

17. The illumination device of claim 16, wherein the flexible elongated member comprises a heat transfer cable therein for conducting heat away from the heat sink.

18. The illumination device of claim 1, further comprising:
 a proximal connector between the control module and the flexible elongated member; and
 a distal connector between the illumination module and the flexible elongated member.

19. The illumination device of claim 18, wherein at least one of the control and illumination modules is removably attached to the flexible elongated member via the proximal and distal connectors, respectively.

20. The illumination device of claim 1, wherein the set of user input elements is configurable for adjusting illuminance of the set of lighting elements.

* * * * *